US012100489B2

United States Patent
Kim et al.

(10) Patent No.: US 12,100,489 B2
(45) Date of Patent: Sep. 24, 2024

(54) SYSTEM AND METHOD FOR MANAGING MEDICAL INFORMATION WITH ENHANCED PERSONAL INFORMATION PROTECTION

(71) Applicant: ICONLOOP Inc., Seoul (KR)

(72) Inventors: Jong Hyup Kim, Gyeonggi-do (KR); Hyeok Gon Ryu, Gyeonggi-do (KR); Moon Kyu Song, Gyeonggi-do (KR)

(73) Assignee: ICONLOOP Inc., Seoul (KR)

( * ) Notice: Subject to any disclaimer, the term of this patent is extended or adjusted under 35 U.S.C. 154(b) by 414 days.

(21) Appl. No.: 17/501,153

(22) Filed: Oct. 14, 2021

(65) Prior Publication Data

US 2022/0165369 A1    May 26, 2022

(30) Foreign Application Priority Data

Nov. 20, 2020  (KR) .......... 10-2020-0156615

(51) Int. Cl.
| | | |
|---|---|---|
| *G16H 10/60* | (2018.01) | |
| *G16H 10/20* | (2018.01) | |
| *H04L 9/00* | (2022.01) | |
| *H04L 9/08* | (2006.01) | |
| *H04L 9/14* | (2006.01) | |
| *H04L 9/32* | (2006.01) | |

(52) U.S. Cl.
CPC .......... *G16H 10/20* (2018.01); *G16H 10/60* (2018.01); *H04L 9/0822* (2013.01); *H04L 9/14* (2013.01); *H04L 9/3236* (2013.01); *H04L 9/50* (2022.05)

(58) Field of Classification Search
CPC ........ G16H 10/20; G16H 10/60; G16B 20/30; H04L 9/0822; H04L 9/14; H04L 9/3236; H04L 9/50; H04L 2209/46; H04L 9/085; H04L 9/0643; H04L 67/1097; H04L 2209/88; G16B 20/00
See application file for complete search history.

(56) References Cited

FOREIGN PATENT DOCUMENTS

| | | | | |
|---|---|---|---|---|
| DE | 102008000348 A1 | * | 8/2009 | .......... G06F 19/322 |
| KR | 10-2012-0002729 A | | 1/2012 | |
| KR | 10-2014-0029984 A | | 3/2014 | |
| KR | 10-1517911 B | | 5/2015 | |
| KR | 10-2017-0074667 A | | 6/2017 | |
| KR | 20210027951 A | * | 9/2019 | |
| KR | 10-2020-0007189 A | | 1/2020 | |
| KR | 10-2020-0016458 A | | 2/2020 | |

OTHER PUBLICATIONS

Maccari, L, et al. "Protecting mobile agents communications in pervasive networks with a trusted distributed mediator for ID-based RSA", Security Comm. Networks, 7:1887-1899, Nov. 18, 2013.

* cited by examiner

*Primary Examiner* — Mohammed Waliullah
(74) *Attorney, Agent, or Firm* — Meunier Carlin & Curfman LLC

(57) ABSTRACT

A system and method for managing medical information with enhanced personal information protection are disclosed. The system and method may generate a distributed key including a user key, an agent key, and a backup key, and manage medical data of a user, using a user agent assigned to each user and the distributed key, to prevent personal information of the user from being directly accessed from outside.

18 Claims, 7 Drawing Sheets

SYSTEM AND METHOD FOR MANAGING MEDICAL INFORMATION WITH ENHANCED PERSONAL INFORMATION PROTECTION

CROSS-REFERENCE TO RELATED APPLICATION

This application claims the benefit of Korean Patent Application No. 10-2020-0156615 filed on Nov. 20, 2020, in the Korean Intellectual Property Office, the entire disclosure of which is incorporated herein by reference for all purposes.

BACKGROUND

1. Field of the Invention

One or more example embodiments relate to a technology for managing medical information with enhanced personal information protection.

2. Description of the Related Art

A considerable amount of time and effort are required to develop a drug for the treatment or prevention of a specific disease, and the development of a therapeutic agent requires clinical trials to identify the efficacy and side effects of a candidate substance that is being studied.

In order to obtain meaningful clinical trial data, a process of recruiting suitable subjects for clinical trials is preceded. An offline clinical trial volunteer recruitment announcement is made for unspecified people or a unilateral clinical trial volunteer recruitment announcement is made using the Internet.

However, it is very difficult to recruit suitable subjects through the offline clinical trial volunteer recruitment announcement within a validity period because access to information is restricted due to regional limitations of a clinical trial hosting medical institution, and the inconvenience of having to go through a basic interview process through telephone counseling and waste of work resources always exist.

In addition, a clinical trial volunteer recruitment announcement through the Internet may overcome the regional limitations. However, there is a short-coming in that it is not possible to filter duplicate volunteers due to non-sharing of clinical trial volunteer information between clinical trial hosting medical institutions.

There is another method in which hospital officials input medical records of patients into a database and extract clinical data from the database.

However, in the above case, personal information of patients who do not wish clinical trials may be leaked, and accordingly it is required to be careful about data management.

Accordingly, there is a need for a method for managing medical information with enhanced personal information protection.

SUMMARY

Example embodiments provide a system and method for managing medical information with enhanced personal information protection.

According to an aspect, there is provided a system for managing medical information with enhanced personal information protection, the system including an agent management unit configured to generate and manage a user agent for each user, a key management unit configured to generate a backup key included in a distributed key, a medical database configured to store final encrypted medical data of a user, and a medical blockchain configured to store a hash value of medical data of the user. The user agent may be configured to generate an agent key included in the distributed key, generate second encrypted medical data by encrypting medical data with the agent key when first encrypted medical data generated by encrypting the medical data with a user key included in the distributed key is received together with the medical data from a user terminal, generate the final encrypted medical data using the first encrypted medical data and the second encrypted medical data, store the final encrypted medical data in the medical database, and generate a hash value of the medical data and store the hash value of the medical data in the medical blockchain.

At this time, the medical data may include at least one of health checkup data of the user, a prescription of the user, genetic analysis information of the user, exercise information of the user, hospital care data of the user, and lifelog information of the user.

At this time, when a query of stored medical data is requested by the user terminal, the user agent may be configured to generate second decrypted medical data by decrypting the final encrypted medical data stored in the medical database with the agent key, and transmit, to the user terminal, the second decrypted medical data and the final encrypted medical data. When the second decrypted medical data and the final encrypted medical data are received, the user terminal may be configured to generate first decrypted medical data by decrypting the final encrypted medical data with the user key, and obtain decrypted medical data using the first decrypted medical data and the second decrypted medical data.

At this time, the agent management unit may be configured to generate and manage a hospital agent for each hospital. The hospital agent may be configured to transmit, to the user agent, a record request for additional medical data about the user when the record request is received from a hospital, identify the user through a verifiable credential of the user consenting to recording when the verifiable credential is received from the user agent, and transmit additional medical data of the user to the user agent when the additional medical data is received from the hospital. The user agent may be configured to inquire of the user terminal about the record request when the record request is received, transmit, to the hospital agent, the verifiable credential of the user consenting to recording when a permission for the record request is received from the user terminal, transmit the additional medical data to the user terminal when the additional medical data is received from the hospital agent, generate second encrypted additional medical data by encrypting the additional medical data with the agent key, generate final encrypted additional medical data using first encrypted additional medical data and the second encrypted additional medical data when the first encrypted additional medical data is received from the user terminal, store the final encrypted additional medical data in the medical database, and generate a hash value of the additional medical data and store the hash value of the additional medical data in the medical blockchain. The user terminal may be configured to generate the first encrypted additional medical data by encrypting the received additional medical data with the user key, and transmit the first encrypted additional medical data to the user agent.

At this time, the agent management unit may be configured to generate and manage a hospital agent for each hospital. The hospital agent may be configured to transmit, to the user agent, a query request for medical information of the user when the query request for medical information is received from a hospital, identify the user through a verifiable credential of the user consenting to the query request for medical information when the verifiable credential is received from the user agent, and request medical data of the user from the user agent. The user agent may be configured to inquire of the user terminal about the query request for medical information, transmit the verifiable credential of the user to the hospital agent when a permission for the query request for medical information is received from the user terminal, transmit the final encrypted medical data to the user terminal when the medical data of the user is requested by the hospital agent, generate second decrypted medical data by decrypting the final encrypted medical data with the agent key, obtain decrypted medical data using first decrypted medical data and the second decrypted medical data when the first decrypted medical data is received from the user terminal, and transmit the decrypted medical data to the hospital agent. When the final encrypted medical data is received, the user terminal may be configured to generate the first decrypted medical data by decrypting the final encrypted medical data with the user key, and transmit the first decrypted medical data to the user agent.

At this time, the agent management unit may be configured to generate and manage a clinical agent for each clinical trial requiring place. The clinical agent may be configured to transmit clinical trial information to all user agents managed by the agent management unit when the clinical trial information is received from a clinical trial requiring place. The user agent may be configured to transmit the final encrypted medical data to the key management unit when the clinical trial information is received, generate second decrypted medical data by decrypting the final encrypted medical data with the agent key, obtain decrypted medical data using first decrypted medical data and the second decrypted medical data when the first decrypted medical data is received from the key management unit, identify whether the user is included in a clinical trial subject required in the clinical trial information using the decrypted medical data, inquire of the user terminal whether to participate in a clinical trial when the user is included in the clinical trial subject, and transmit, to the clinical agent, a verifiable credential of the user or the decrypted medical data when a response indicating participation in the clinical trial is received from the user terminal. The key management unit may be configured to generate first decrypted medical data by decrypting the final encrypted medical data with the backup key when the final encrypted medical data is received, and transmit the first decrypted medical data to the user agent.

At this time, the clinical agent may be configured to transmit, to the user agent, an end message according to an end of the clinical trial when the end message is received from the clinical trial requiring place. The user agent may be configured to transmit the end message to the user terminal when the end message is received.

At this time, the clinical trial information may include at least one of a clinical trial subject condition, a clinical trial description, a clinical trial period, a clinical trial risk, and clinical trial participation fee information.

At this time, the user agent may be configured to inquire of the user terminal whether to participate in the clinical trial, when the user is included in the clinical trial subject and when the clinical trial is included in a permitted clinical trial item preset by the user.

According to another aspect, there is provided a method for managing medical information with enhanced personal information protection in a medical information management system, the method including generating, by a user terminal, a user key included in a distributed key, generating, by a user agent, an agent key included in the distributed key, and generating, by a key management unit, a backup key included in the distributed key, generating, by the user terminal, first encrypted medical data by encrypting medical data with the user key, and transmitting the medical data and the first encrypted medical data to the user agent, generating, by the user agent, second encrypted medical data by encrypting the medical data received from the user terminal with the agent key, generating final encrypted medical data using the first encrypted medical data and the second encrypted medical data, and storing the final encrypted medical data in a medical database, and generating, by the user agent, a hash value of the received medical data and storing the hash value of the received medical data in a medical blockchain.

At this time, the medical data may include at least one of health checkup data of the user, a prescription of the user, genetic analysis information of the user, exercise information of the user, hospital care data of the user, and lifelog information of the user.

At this time, the method may further include, when a query of stored medical data is requested by the user terminal, generating, by the user agent, second decrypted medical data by decrypting the final encrypted medical data stored in the medical database with the agent key, and transmitting, to the user terminal, the second decrypted medical data and the final encrypted medical data, and when the second decrypted medical data and the final encrypted medical data are received, generating, by the user terminal, first decrypted medical data by decrypting the final encrypted medical data with the user key, and obtaining decrypted medical data using the first decrypted medical data and the second decrypted medical data.

At this time, the method may further include transmitting, by a hospital agent, a record request from a hospital to the user agent, inquiring, by the user agent, of the user terminal about the record request, and transmitting, to the hospital agent, a verifiable credential of the user consenting to recording when a permission for the record request is received from the user terminal, identifying, by the hospital agent, the user through the verifiable credential of the user, and transmitting additional medical data of the user to the user agent when the additional medical data is received from the hospital, transmitting, by the user agent, the additional medical data to the user terminal, and generating second encrypted additional medical data by encrypting the additional medical data with the agent key, generating, by the user terminal, first encrypted additional medical data by encrypting the additional medical data with the user key, and transmitting the first encrypted additional medical data to the user agent, and generating, by the user agent, final encrypted additional medical data using the first encrypted additional medical data and the second encrypted additional medical data, storing the final encrypted additional medical data in the medical database, and generating a hash value of the additional medical data and storing the hash value of the additional medical data in the medical blockchain.

At this time, the method may further include transmitting, by a hospital agent, a query request for medical information of the user from a hospital to the user agent, inquiring, by the user agent, of the user terminal about the query request for medical information, and transmitting, to the hospital agent, a verifiable credential of the user consenting to the query request for medical information when a permission for the query request for medical information is received from the user terminal, identifying, by the hospital agent, the user through the verifiable credential, and requesting medical data of the user from the user agent, transmitting, by the user agent, the final encrypted medical data to the user terminal when the medical data of the user is requested by the hospital agent, generating, by the user terminal, first decrypted medical data by decrypting the final encrypted medical data with the user key, and transmitting the first decrypted medical data to the user agent, and generating, by the user agent, second decrypted medical data by decrypting the final encrypted medical data with the agent key, obtaining decrypted medical data using the first decrypted medical data and the second decrypted medical data, and transmitting the decrypted medical data to the hospital agent.

At this time, the method may further include transmitting, by a clinical agent, clinical trial information to all user agents when the clinical trial information is received, transmitting, by the user agent, the final encrypted medical data to the key management unit when the clinical trial information is received, generating, by the key management unit, first decrypted medical data by decrypting the final encrypted medical data with the backup key, and transmitting the first decrypted medical data to the user agent, generating, by the user agent, second decrypted medical data by decrypting the final encrypted medical data with the agent key, and obtaining decrypted medical data using the first decrypted medical data and the second decrypted medical data, identifying, by the user agent, whether the user is included in a clinical trial subject required in the clinical trial information using the decrypted medical data, inquiring, by the user agent, of the user terminal whether to participate in a clinical trial when the user is included in the clinical trial subject, and transmitting, by the user agent, a verifiable credential of the user or the decrypted medical data to the clinical agent when a response indicating participation in the clinical trial is received from the user terminal.

At this time, the method may further include transmitting, by the clinical agent, an end message according to an end of the clinical trial to the user agent when the end message is received, and transmitting, by the user agent, the end message to the user terminal when the end message is received.

At this time, the clinical trial information may include at least one of a clinical trial subject condition, a clinical trial description, a clinical trial period, a clinical trial risk, and clinical trial participation fee information.

At this time, the inquiring, by the user agent, of the user terminal whether to participate in the clinical trial when the user is included in the clinical trial subject may include inquiring, by the user agent, of the user terminal whether to participate in the clinical trial, when the user is included in the clinical trial subject and when the clinical trial is included in a permitted clinical trial item preset by the user.

Additional aspects of example embodiments will be set forth in part in the description which follows and, in part, will be apparent from the description, or may be learned by practice of the disclosure.

According to example embodiments, the system and method for managing medical information with enhanced personal information protection may generate a distributed key including a user key, an agent key, and a backup key, and manage medical data of a user, using a user agent assigned to each user and the distributed key, thereby making it impossible to directly access personal information of the user from outside, and allowing a person who intends to participate in a clinical trial to easily participate.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
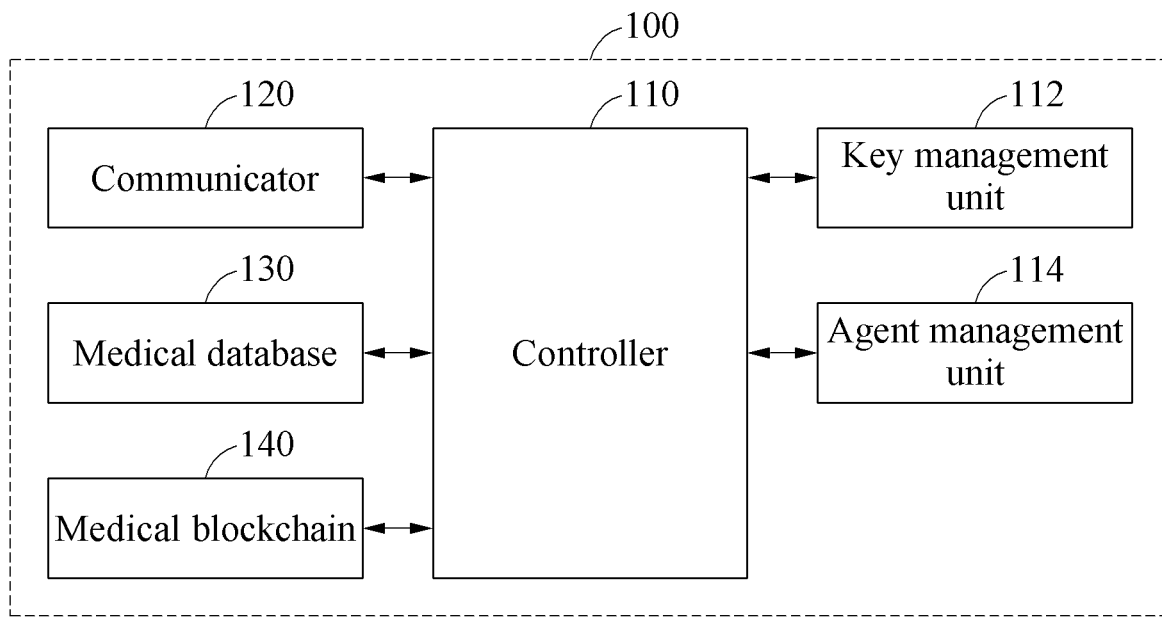
FIG. 1 is a diagram illustrating a medical information management system according to an example embodiment.

Hereinafter, example embodiments will be described in detail with reference to the accompanying drawings. However, various modifications may be made to the example embodiments, and thus, the scope of the patent application should not be construed as limited to the example embodiments set forth herein. It should be understood that all changes, equivalents, and replacements to the example embodiments are included within the scope.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, operations, elements, and/or components, but do not preclude the presence or addition of one or more other features, integers, operations, elements, components, and/or groups thereof.

Unless otherwise defined, all terms, including technical and scientific terms, used herein have the same meaning as commonly understood by those skilled in the art to which the example embodiments pertain. Terms, such as those defined in commonly used dictionaries, are to be interpreted as having a meaning that is consistent with their meaning in the context of the relevant art, and are not to be interpreted in an idealized or overly formal sense unless expressly so defined herein.

In addition, in the description with reference to the accompanying drawings, the same components are assigned with the same reference numerals regardless of the numerals in the drawings, and the redundant description thereof will be omitted. In the description of example embodiments, a detailed description of a well-known related technology will be omitted when it is deemed that such description will unnecessarily obscure the gist of the example embodiments.

In addition, it will be understood that, although the terms first, second, A, B, (a), (b), and the like may be used herein to describe various components of the example embodiments, these terms are only used to distinguish one component from another component and essential, order, or sequence of corresponding components are not limited by these terms. It will be understood that when one component is referred to as being "connected to", "coupled to", or "linked to" another component, one component may be "connected to", "coupled to", or "linked to" another component via a further component although one component may be directly connected to or directly linked to another component.

The same name may be used to describe a component included in an example embodiment and a component having a common function in another example embodiment. Unless otherwise mentioned, a description on an example embodiment may be applicable to another example embodiment and thus, a duplicated description will be omitted for conciseness.

Hereinafter, a system and method for managing medical information with enhanced personal information protection according to an example embodiment will be described in detail with reference to FIGS. 1 to 7.

FIG. 1 is a diagram illustrating a medical information management system according to an example embodiment.

Figure 2:
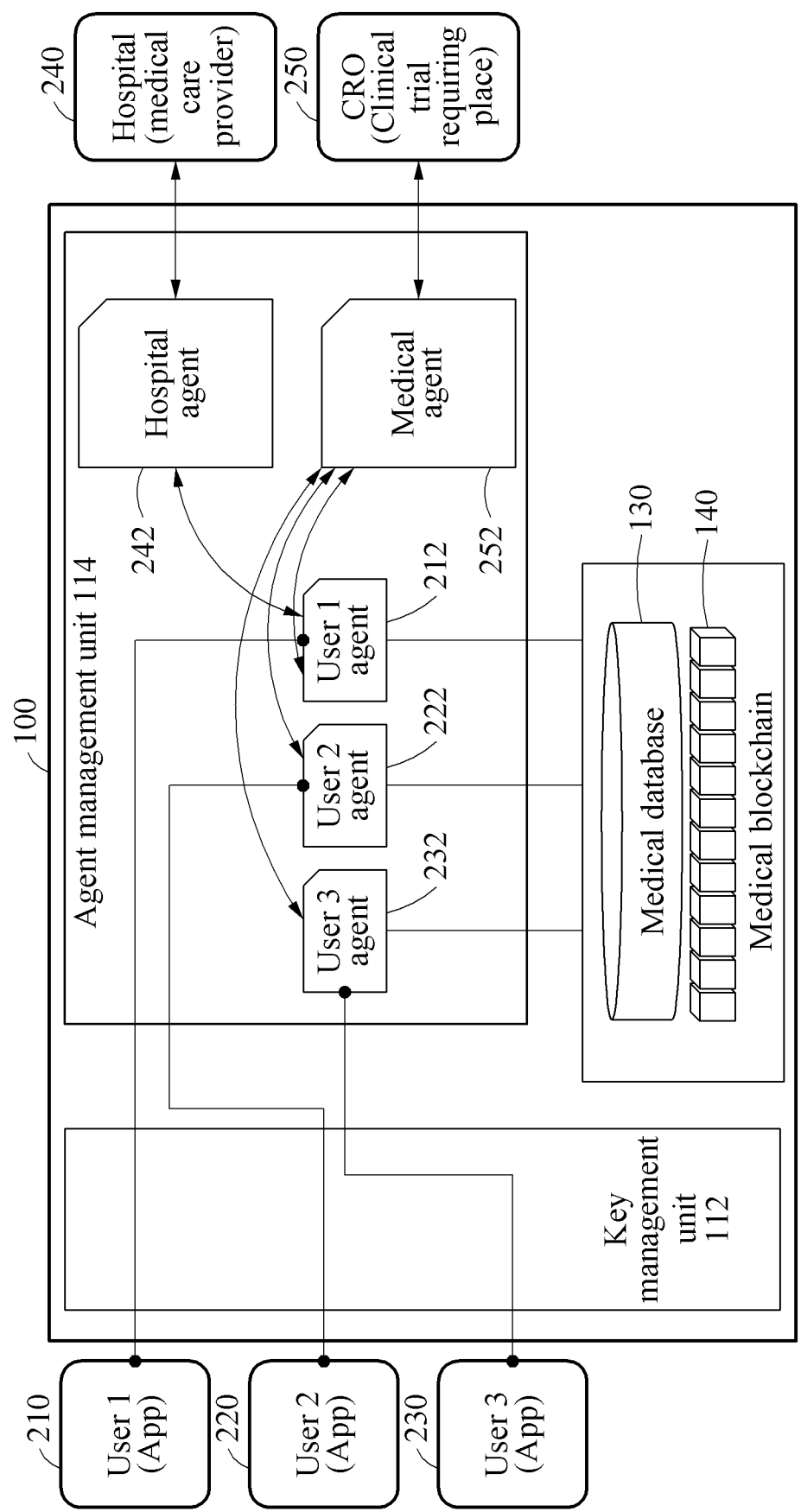
FIG. 2 is a diagram illustrating a connection relationship between a medical information management system and a user terminal, a hospital, and a clinical trial requiring place according to an example embodiment.

FIG. 2 is a diagram illustrating a connection relationship between a medical information management system and a user terminal, a hospital, and a clinical trial requiring place according to an example embodiment.

Referring to FIGS. 1 and 2, a medical information management system 100 may include a controller 110, a key management unit 112, an agent management unit 114, a communicator 120, a medical database 130, and a medical blockchain 140.

The communicator 120, which is a communication interface device including a receiver and a transmitter, may transmit and receive data in a wired or wireless manner. The communicator 120 may communicate with user terminals 210, 220, and 230, a hospital terminal 240, and a clinical trial requiring place 250.

The medical database 130 may store encrypted medical data of a user for each user.

The medical blockchain 140 may store a hash value of medical data of the user.

At this time, as the hash value of the medical data is stored in the medical blockchain 140, the medical information management system 110 may compare a hash value generated using the medical data stored in the medical database 130 and the hash value of the medical data stored in the medical blockchain 140 to each other, thereby identifying whether the medical data of the user is correct or maliciously changed.

The key management unit 112 may generate a backup key included in a distributed key by means of a secure multi-party computation (sMPC) technique.

The agent management unit 114 may respectively generate and manage user agents 212, 222, and 232 for the user terminals 210, 220, and 230, generate and manage a hospital agent 242 for each hospital 240, and generate and manage a clinical agent 252 for each clinical trial requiring place 250. At this time, the user agents 212, 222, and 232, the hospital agent 242, and the clinical agent 252 may be a type of program driven by the controller 110.

Each of the user agents 212, 222, and 232 may generate an agent key included in the distributed key by means of the sMPC technique. When medical data and first encrypted medical data are received from each of the user terminals 210, 220, and 230, each of the user agents 212, 222, and 232 may generate second encrypted medical data by encrypting the medical data with the agent key, generate final encrypted medical data using the first encrypted medical data and the second encrypted medical data, store the final encrypted medical data in the medical database 130, and generate and store a hash value of the received medical data in the medical blockchain 140.

At this time, the first encrypted medical data, the second encrypted medical data, and the final encrypted medical data may be generated using the sMPC technique.

In addition, the medical data may include at least one health checkup data of the user, a prescription of the user, genetic analysis information of the user, exercise information of the user, hospital care data of the user, and lifelog information of the user. Here, the life log information of the user may be information about the number of steps, a blood pressure, a pulse rate, an electrocardiogram, and the like measured by the user while living.

Each of the user terminals 210, 220, and 230 may generate a user key included in the distributed key by means of the sMPC technique, generate first encrypted medical data by encrypting the medical data with the user key included in the distributed key, and transmit the medical data and the first encrypted medical data to the user agents 212, 222, and 232 respectively corresponding to the user terminals 210, 220, and 230.

Hereinafter, with reference to various example embodiments, operations of the user agents 212, 222, and 232, and the hospital agent 242 or the clinical agent 252 will be described in more detail.

In an example embodiment, when the first user 210 intends to query medical data, the first user agent 212 may operate as follows.

When a query of stored medical data is requested by the first user terminal 210, the first user agent 212 may generate second decrypted medical data by decrypting the final encrypted medical data stored in the medical database 130 with the agent key, and transmit the second decrypted medical data and the final encrypted medical data to the first user terminal 210.

When the second decrypted medical data and the final encrypted medical data are received from the first user agent 212, the first user terminal 210 may generate first decrypted medical data by decrypting the final encrypted medical data with the user key, and obtain decrypted medical data using the first decrypted medical data and the second decrypted medical data.

At this time, the first decrypted medical data, the second decrypted medical data, and the decrypted medical data may be generated using the sMPC technique.

In an example embodiment, when the hospital 240 intends to store a medical record of the first user 210, the hospital agent 242 and the first user agent 212 may operate as follows.

When a record request for additional medical data about the user is received from the hospital 240, the hospital agent 242 may transmit the record request to the first user agent 212. When a verifiable credential of the user consenting to recording is received from the first user agent 212, the hospital agent 242 may identify the user through the verifiable credential. When additional medical data of the user is received from the hospital 240, the hospital agent 242 may transmit the additional medical data of the user to the first user agent 212. At this time, the verifiable credential of the user may be received by a user agent together with a permission for a query request for medical information from a user terminal, or may be a credential received and managed by the user agent in advance.

The hospital 240 may transmit the record request for additional medical data to the hospital agent 242, but may provide a QR code for requesting the recording of medical data to the user of the first user terminal 210. When the user scans the QR code through an application, a message that permits recording may be processed to be directly transmitted to the user agent 212. When using the QR code as described above, a process of transmitting, by the hospital 240, the record request, and transmitting, by the hospital agent 242, the record request to the first user agent 212 may be omitted.

When the record request is received, the first user agent 212 may inquire of the first user terminal 210 about the record request. When a permission for the record request is received from the first user terminal 210, the first user agent 212 may transmit the verifiable credential of the user consenting to recording to the hospital agent 242, and receive the additional medical data of the user from the hospital agent 242. When the additional medical data of the user is received, the first user agent 212 may transmit the additional medical data to the first user terminal 210, and generate second encrypted additional medical data by encrypting the additional medical data with the agent key. When first encrypted additional medical data is received from the first user terminal 210, the first user agent 212 may generate final encrypted additional medical data using the first encrypted additional medical data and the second encrypted additional medical data, store the final encrypted additional medical data in the medical database 130, and generate a hash value of the additional medical data and store the hash value in the medical blockchain 140.

The first user terminal 210 may generate the first encrypted additional medical data by encrypting the received additional medical data with the user key, and transmit the first encrypted additional medical data to the first user agent 212.

At this time, the first encrypted additional medical data, the second encrypted additional medical data, and the final encrypted additional medical data may be generated using the sMPC technique.

In an example embodiment, when the hospital 240 intends to check medical data of the first user 210 stored in the medical database 130, the hospital agent 242 and the first user agent 212 may operate as follows.

When a query request for medical information of the user is received from the hospital 240, the hospital agent 242 may transmit the query request for medical information to the first user agent 212. When a verifiable credential of the user consenting to the query request for medical information is received from the first user agent 212, the hospital agent 242 may identify the user through the verifiable credential, and may request medical data of the user from the first user agent 212.

The hospital 240 may transmit the query request for medical information of the user to the hospital agent 242, but may provide the user 210 with a QR code for requesting user medical information query. When the user scans the QR code through an application, a message that permits the user medical information query may be processed to be directly transmitted to the user agent 212. When using the QR code as described above, a process of transmitting, by the hospital 240, the query request for medical information of the user, and transmitting, by the hospital agent 242, the query request for medical information of the user to the first user agent 212 may be omitted.

The first user agent 212 may inquire of the first user terminal 210 about the query request for medical information. When a permission for the query request for medical information is received from the first user terminal 210, the first user agent 212 may transmit the verifiable credential of the user to the hospital agent 242. When the medical data of the user is requested by the hospital agent 242, the first user agent 212 may transmit final encrypted medical data to the first user terminal 210, and generate second decrypted medical data by decrypting the final encrypted medical data with the agent key. When first decrypted medical data is received from the first user terminal 210, the first user agent 212 may obtain decrypted medical data using the first decrypted medical data and the second decrypted medical data, and transmit the decrypted medical data to the hospital agent 242.

When the final encrypted medical data is received, the first user terminal 210 may generate the first decrypted medical data by decrypting the final encrypted medical data with the user key, and transmit the first decrypted medical data to the first user agent 212.

At this time, the first decrypted medical data, the second decrypted medical data, and the decrypted medical data may be generated using the sMPC technique.

In an example embodiment, when the clinical trial requiring place 250 intends to identify whether to participate in a clinical trial and manage the clinical trial, the clinical agent 252 and the user agents 212, 222, and 232 may operate as follows.

When clinical trial information is received from the clinical trial requiring place 250, the clinical agent 252 may transmit the clinical trial information to all user agents managed by an agent management unit. When the verifiable credential of the user or the decrypted medical data of the user is received from the user agents 212, 222, and 232, the clinical agent 252 may identify the user, and provide the decrypted medical data of the user to the clinical trial requiring place 250. At this time, the clinical trial information may include at least one of a clinical trial subject condition, a clinical trial description, a clinical trial period, a clinical trial risk, and clinical trial participation fee information.

In addition, when an end message according to an end of the clinical trial is received from the clinical trial requiring place 250, the clinical agent 252 may transmit the end message to a user agent of the ended user. At this time, the end message may include information about a result of the clinical trial, information about a participation fee for participating in the clinical trial, or the like.

When the clinical trial information is received from the clinical agent 252, the user agents 212, 222, and 232 may transmit the final encrypted medical data to the key management unit 112, and generate the second decrypted medical data by decrypting the final encrypted medical data with the agent key. When the first decrypted medical data is received from the key management unit 112, the user agents 212, 222, and 232 may obtain the decrypted medical data using the first decrypted medical data and the second decrypted medical data, and identify whether the user is included in a clinical trial subject required in the clinical trial information using the decrypted medical data. When the user is included in the clinical trial subject, the user agents 212, 222, and 232 may inquire of a corresponding user terminal whether to participate in the clinical trial. When a response indicating participation in the clinical trial is received from the user terminal, the user agents 212, 222, and 232 may inquire of the corresponding user terminals 210, 220, and 230 whether to participate in the clinical trial. When a response indicating participation in the clinical trial is received from the user terminals 210, 220, and 230, the user agents 212, 222, and 232 may transmit the verifiable credential of the user or the decrypted medical data of the user to the clinical agent 252.

When the user agents 212, 222, and 232 inquires of the user terminals 210, 220, and 230 whether to participate in the clinical trial, the user agents 212, 222, and 232 may be allowed to inquire of the user terminals 210, 220, and 230 whether to participate in the clinical trial only in case that the clinical trial is included in a permitted clinical trial item preset by the user in addition to that the user is included in the clinical trial subject.

In addition, when the end message is received from the clinical agent 252, the user agents 212, 222, and 232 may transmit the end message to the user terminals 210, 220, and 230. When the final encrypted medical data is received, the key management unit 112 may generate the first decrypted medical data by decrypting the final encrypted medical data with the backup key, and transmit the first decrypted medical data to the user agents 212, 222, and 232.

At this time, the first decrypted medical data, the second decrypted medical data, and the decrypted medical data may be generated using the sMPC technique.

The controller 110 may control an overall operation of the medical information management system 100. In addition, the controller 110 may perform functions of the key management unit 112 and the agent management unit 114. The controller 110, the key management unit 112, and the agent management unit 114 are separately illustrated to describe respective functions in a distinguished manner. Accordingly, the controller 110 may include at least one processor configured to perform the respective functions of the key management unit 112 and the agent management unit 114. In addition, the controller 110 may include at least one processor configured to perform some of the respective functions of the key management unit 112 and the agent management unit 114.

Hereinafter, a method according to example embodiments configured as described above will be described below with reference to the drawings.

Figure 3:
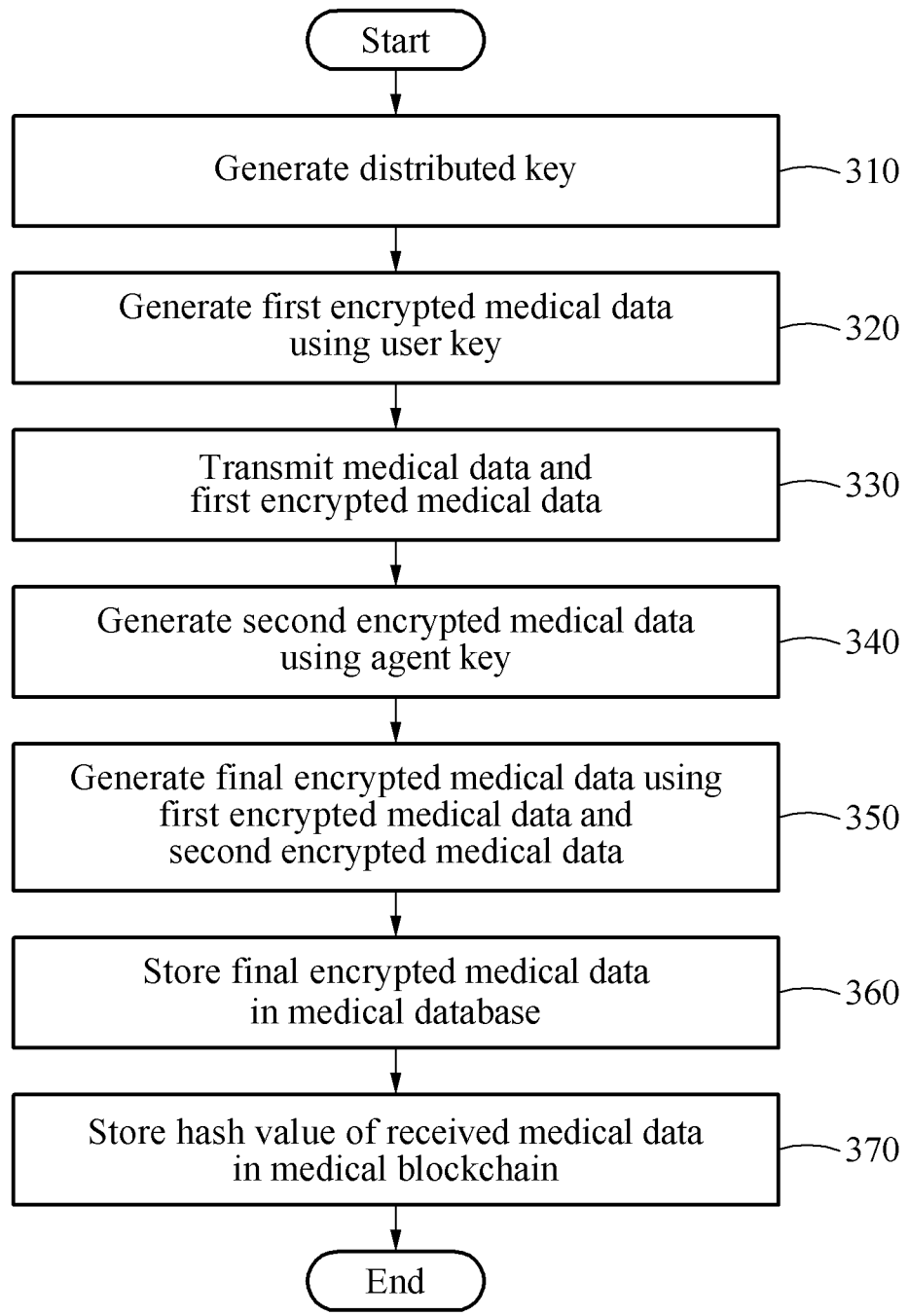
FIG. 3 is a flowchart illustrating a process of storing medical data in a medical information management system according to an example embodiment.

FIG. 3 is a flowchart illustrating a process of storing medical data in a medical information management system according to an example embodiment.

Referring to FIG. 3, in operation 310, a user terminal may generate a user key included in a distributed key, a user agent of the medical information management system 110 may generate an agent key included in the distributed key, and the key management unit 112 of the medical information management system 110 may generate a backup key included in the distributed key.

In operation 320, the user terminal may generate first encrypted medical data by encrypting medical data with the user key.

In operation 330, the user terminal may transmit the medical data and the first encrypted medical data to the user agent.

In operation 340, the user agent may generate second encrypted medical data by encrypting the medical data received from the user terminal with the agent key.

In operation 350, the user agent may generate final encrypted medical data using the first encrypted medical data and the second encrypted medical data.

In operation 360, the user agent may store the final encrypted medical data in the medical database 130.

At this time, the user agent may be an agent program that is generated for each user and manages medical data of a user. In addition, the medical data may include at least one of health checkup data of the user, a prescription of the user, genetic analysis information of the user, exercise information of the user, hospital care data of the user, and lifelog information of the user.

In operation 370, the user agent may generate a hash value of the received medical data and store the hash value of the received medical data in a medical blockchain 140.

The medical information management system 110 may identify whether the medical data of the user is correct or maliciously changed by storing the hash value of the medical data in the medical blockchain 140.

Figure 4:
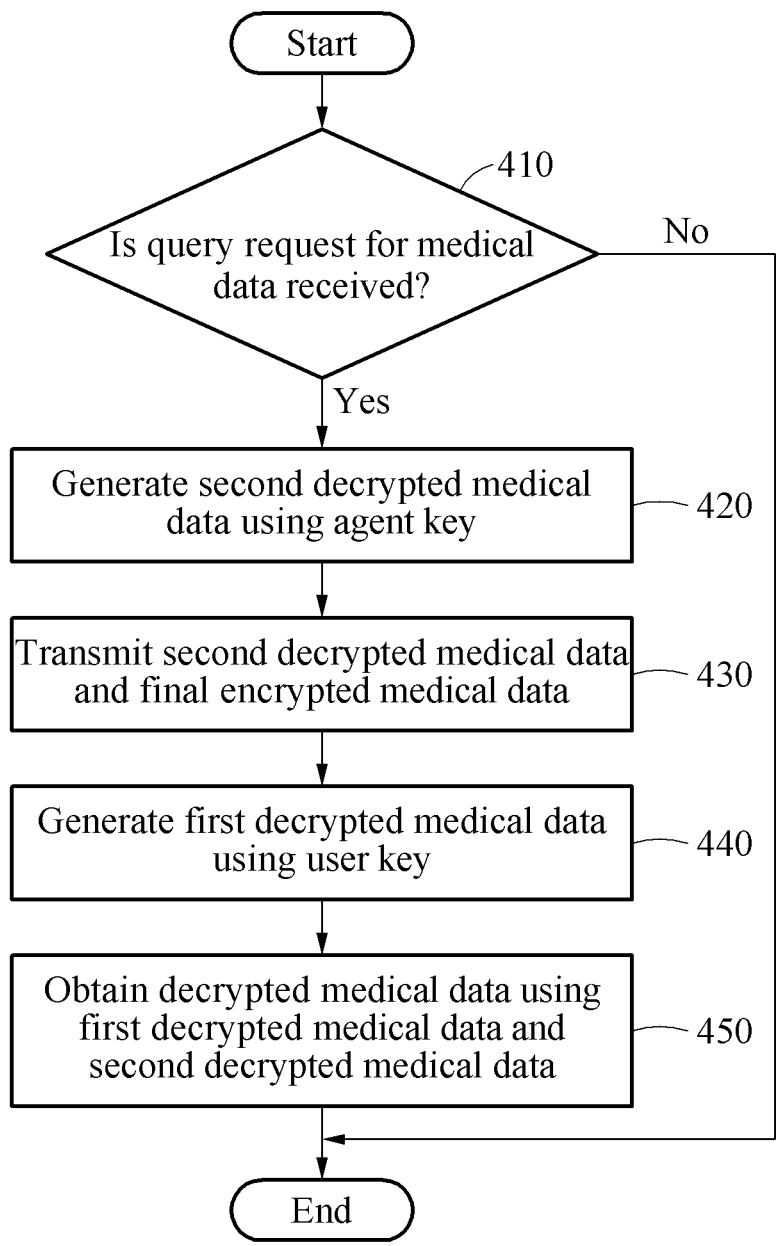
FIG. 4 is a flowchart illustrating a process of processing a query of medical data from a user in a medical information management system according to an example embodiment.

FIG. 4 is a flowchart illustrating a process of processing a query of medical data from a user in a medical information management system according to an example embodiment.

Referring to FIG. 4, when a query of stored medical data is received together with a user key from a user terminal in operation 410, a user agent of the medical information management system 110 may generate second decrypted medical data by decrypting final encrypted medical data stored in the medical database 140 with an agent key in operation 420.

In operation 430, the user agent may transmit the second decrypted medical data and the final encrypted medical data to the user terminal.

In operation 440, when the second decrypted medical data and the final encrypted medical data are received, the user terminal may generate first decrypted medical data by decrypting the final encrypted medical data with the user key.

In operation 450, the user terminal may obtain decrypted medical data using the first decrypted medical data and the second decrypted medical data.

Figure 5:
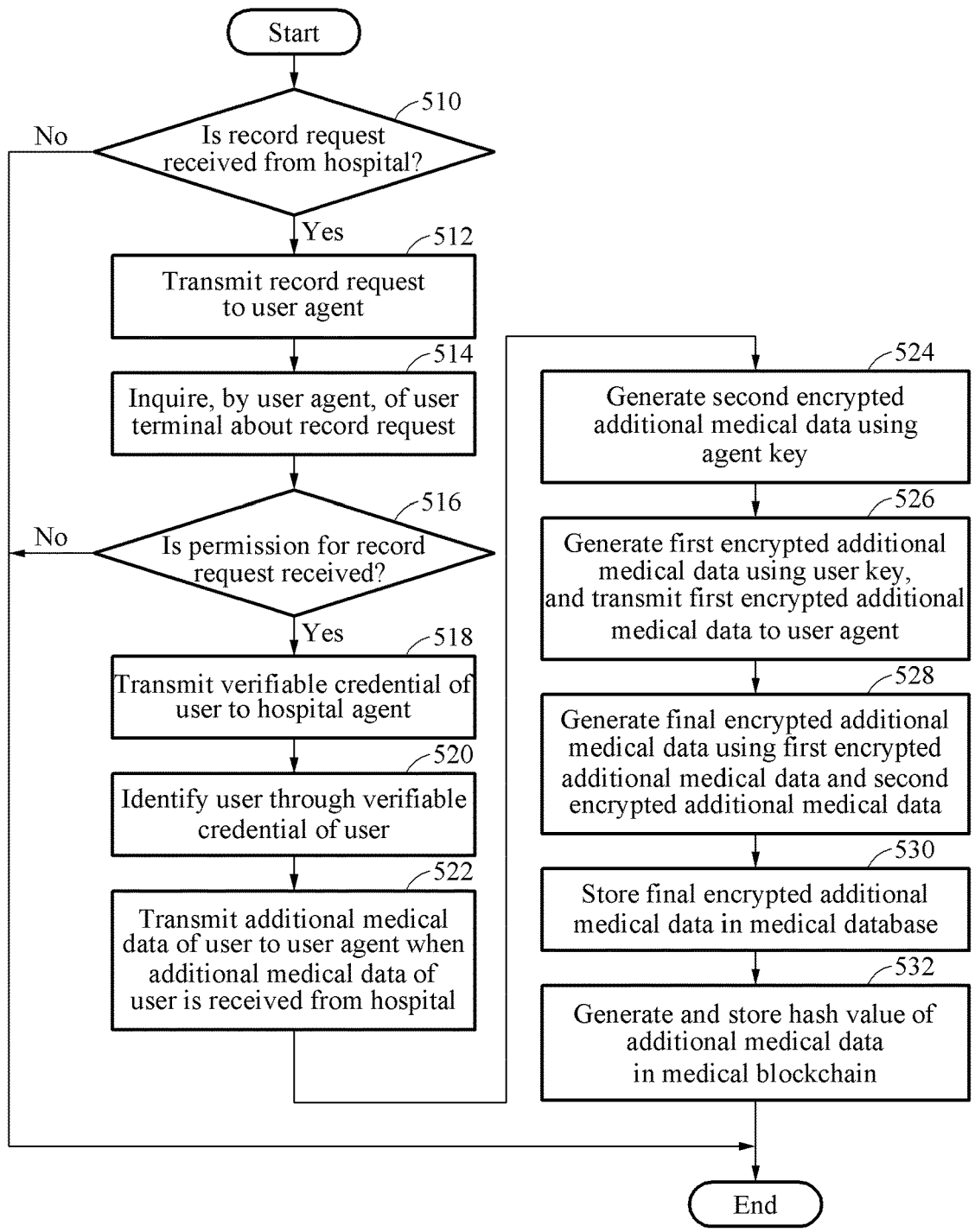
FIG. 5 is a flowchart illustrating a process of processing a record request of a hospital in a medical information management system according to an example embodiment.

FIG. 5 is a flowchart illustrating a process of processing a record request of a hospital in a medical information management system according to an example embodiment.

Referring to FIG. 5, when a hospital agent of the medical information management system 110 receives a record request from a hospital in operation 510, the hospital agent may transmit the record request from the hospital to a user agent in operation 512.

In operation 514, the user agent of the medical information management system 110 may inquire of a user terminal about the record request.

Instead of operations 510 to 514, the hospital 240 may provide the user 210 with a QR code for requesting the recording of medical data, and when the user scans the QR code through an application, a message that permits recording may be directly transmitted to the user agent 212.

When a permission for the record request including a user key is received from the user terminal in operation 516, the user agent of the medical information management system 110 may transmit a verifiable credential of a user consenting to recording to the hospital agent in operation 518.

In operation 520, the hospital agent of the medical information management system 110 may identify the user through the verifiable credential of the user.

In operation 522, when additional medical data of the user is received from the hospital, the hospital agent of the medical information management system 110 may transmit the additional medical data to the user agent.

In operation 524, the user agent of the medical information management system 110 may transmit the additional medical data to the user terminal, and generate second encrypted additional medical data by encrypting the additional medical data with an agent key.

In operation 526, the user terminal may generate first encrypted additional medical data by encrypting the additional medical data with the user key, and transmit the first encrypted additional medical data to the user agent.

In operation 528, the user agent of the medical information management system 110 may generate final encrypted additional medical data using the first encrypted additional medical data and the second encrypted additional medical data.

In operation 530, the user agent of the medical information management system 110 may store the final encrypted additional medical data in the medical database 130.

In operation 532, the user agent of the medical information management system 110 may generate a hash value of the additional medical data and store the hash value of the additional medical data in the medical blockchain 140.

Figure 6:
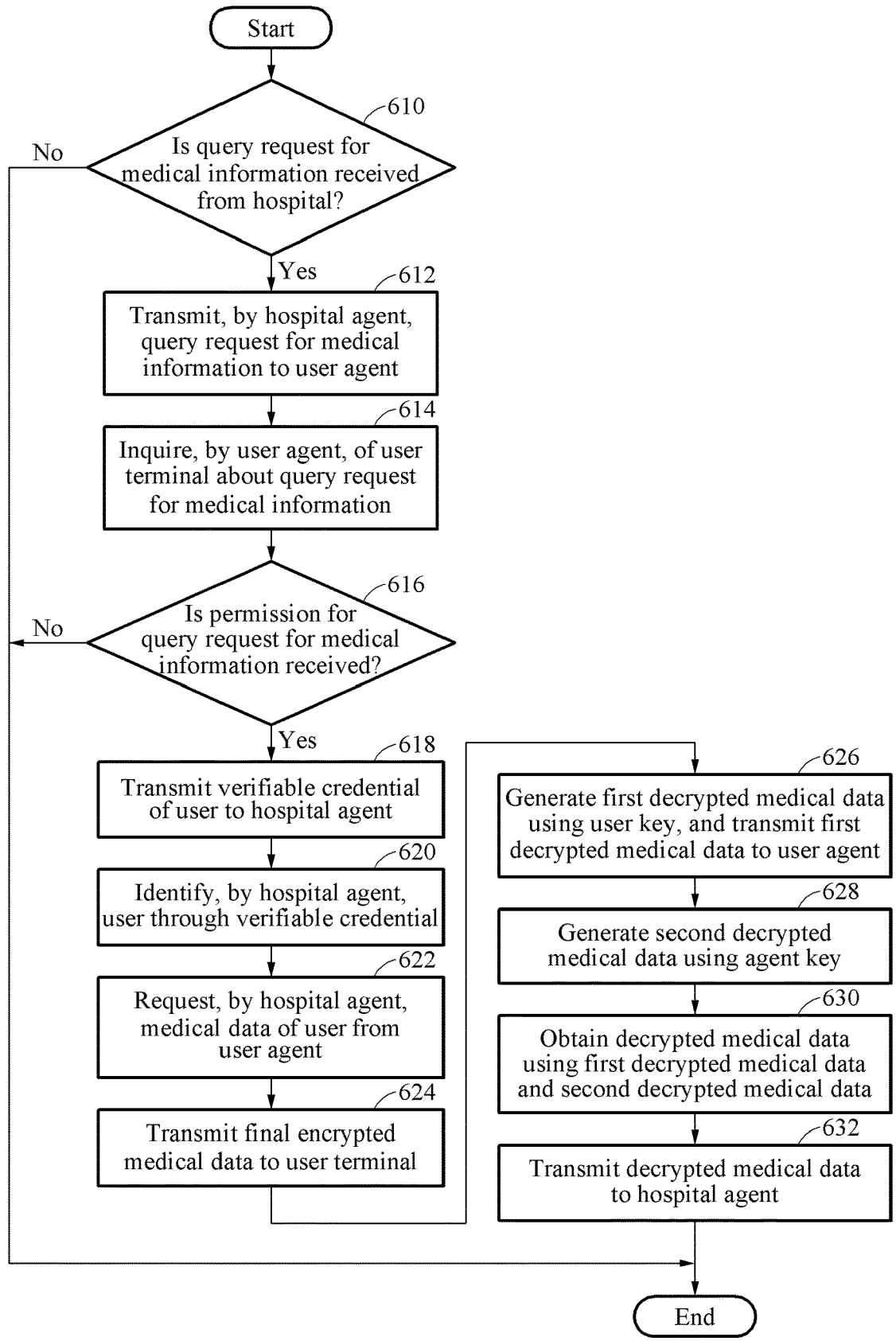
FIG. 6 is a flowchart illustrating a process of processing a query of medical data from a hospital in a medical information management system according to an example embodiment.

FIG. 6 is a flowchart illustrating a process of processing a query of medical data from a hospital in a medical information management system according to an example embodiment.

Referring to FIG. 6, when a query request for medical information of a user is received from a hospital in operation 610, a hospital agent of the medical information management system 110 may transmit the query request for medical information of the user to a user agent in operation 612.

In operation 614, a user agent of the medical information management system 110 may inquire of a user terminal about the query request for medical information.

When a permission for the query request for medical information is received from the user terminal in operation 616, the user agent of the medical information management system 110 may transmit a verifiable credential of the user consenting to the query request for medical information to the hospital agent in operation 618. At this time, the verifiable credential of the user may be received by the user agent together with the permission for the query request for medical information from the user terminal, or may be a credential received and managed by the user agent in advance.

Instead of operations 610 to 616, the hospital 240 may provide the user 210 with a QR code for requesting user medical information query, and when the user scans the QR code through an application, a message that permits the user medical information query may be directly transmitted to the user agent 212.

In operation 620, the hospital agent of the medical information management system 110 may identify the user through the verifiable credential.

In operation 622, the hospital agent of the medical information management system 110 may request medical data of the user from the user agent.

In operation 624, the user agent of the medical information management system 110 may retrieve final encrypted medical data stored in the medical database 130, and transmit the final encrypted medical data to the user terminal.

In operation 626, when the final encrypted medical data is received, the user terminal may generate first decrypted medical data by decrypting the final encrypted medical data with a user key, and transmit the first decrypted medical data to the user agent.

In operation 628, the user agent of the medical information management system 110 may generate second decrypted medical data by decrypting the final encrypted medical data with an agent key.

In operation 630, the user agent of the medical information management system 110 may obtain decrypted medical data using the first decrypted medical data and the second decrypted medical data.

In operation 632, the user agent of the medical information management system 110 may transmit the decrypted medical data to the hospital agent.

Figure 7:
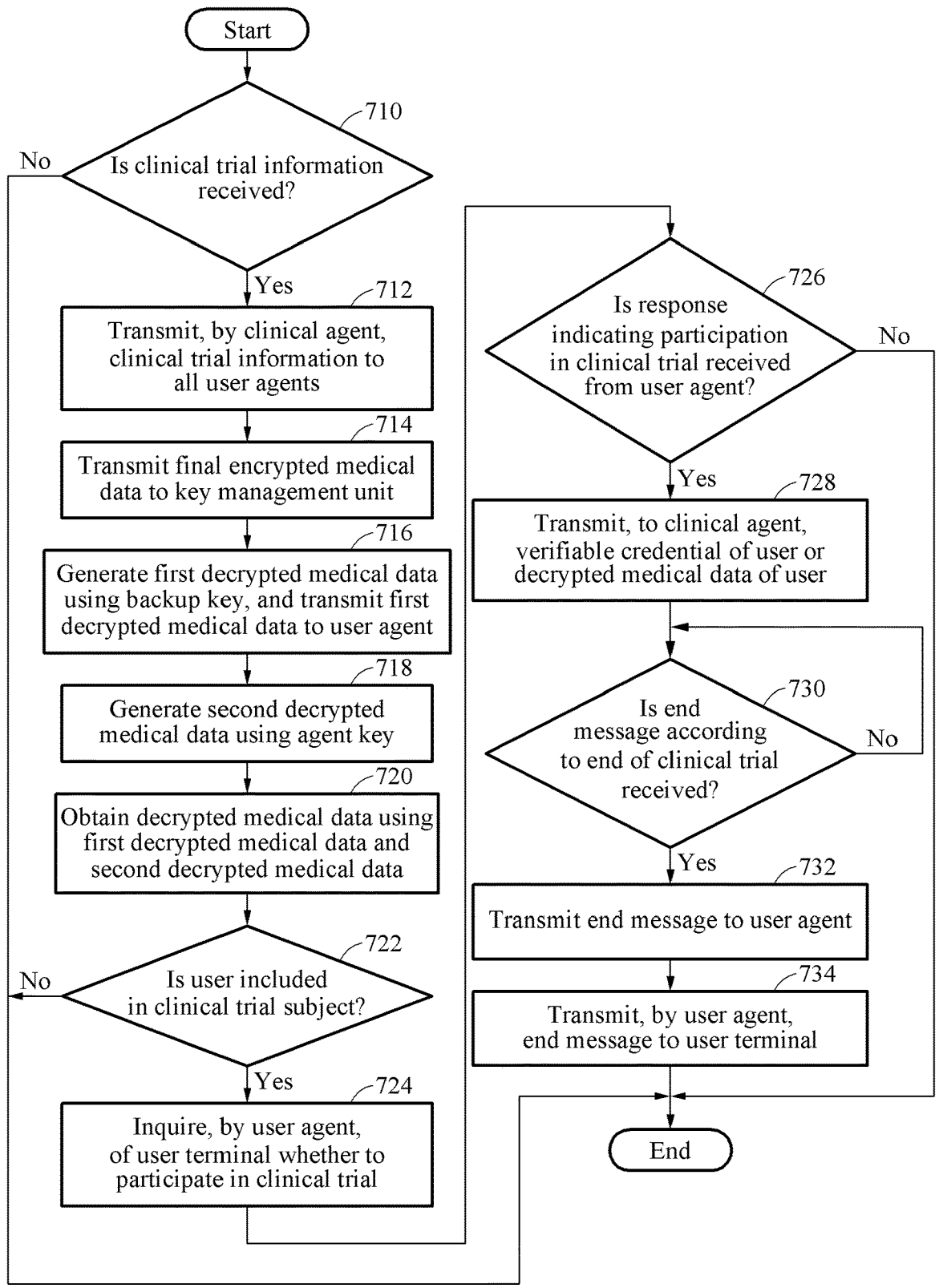
FIG. 7 is a flowchart illustrating an information processing process for a clinical trial in a medical information management system according to an example embodiment.

FIG. 7 is a flowchart illustrating an information processing process for a clinical trial in a medical information management system according to an example embodiment.

Referring to FIG. 7, when clinical trial information is received in operation 710, a clinical agent of the medical information management system 110 may transmit the clinical trial information to all user agents in operation 712.

At this time, the clinical trial information may include at least one of a clinical trial subject condition, a clinical trial description, a clinical trial period, a clinical trial risk, and clinical participation fee information.

In operation 714, when the clinical trial information is received, a user agent of the medical information management system 110 may retrieve final encrypted medical data stored in the medical database 130, and transmit the final encrypted medical data to the key management unit 112.

In operation 716, the key management unit 112 of the medical information management system 110 may generate first decrypted medical data by decrypting the final encrypted medical data with a backup key, and transmit the first decrypted medical data to the user agent.

In operation 718, the user agent of the medical information management system 110 may generate second decrypted medical data by decrypting the final encrypted medical data with an agent key.

In operation 720, the user agent of the medical information management system 110 may obtain decrypted medical data using the first decrypted medical data and the second decrypted medical data.

In operation 722, the user agent of the medical information management system 110 may identify whether a user is included in a clinical trial subject required in the clinical trial information using the decrypted medical data.

When the user is included in the clinical trial subject as a result of identifying in operation 722, the user agent of the medical information management system 110 may inquire of a user terminal whether to participate in a clinical trial in operation 724. At this time, when inquiring of the user terminal whether to participate in the clinical trial in operation 724, the user agent may inquire of the user terminal whether to participate in the clinical trial only in case that the user is included in the clinical trial subject, and the clinical trial is included in a permitted clinical trial item preset by the user.

When a response indicating participation in the clinical trial is received from the user terminal in operation 726, the user agent of the medical information management system 110 may transmit, to a clinical agent, a verifiable credential of the user or decrypted medical data of the user in operation 728.

When an end message according to an end of the clinical trial is received in operation 730, the clinical agent of the medical information management system 110 may transmit the end message to the user agent in operation 732.

In operation 734, when the end message is received, the user agent of the medical information management system 110 may transmit the end message to the user terminal. At this time, the end message may include information about a result of the clinical trial, information about a participation fee for participating in the clinical trial, or the like.

The methods according to the example embodiments may be recorded in non-transitory computer-readable media including program instructions to implement various operations of the example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method for managing medical information with enhanced personal information protection in a medical information management system, the method comprising:
   generating, by a user terminal, a user key included in a distributed key, generating, by a user agent, an agent key included in the distributed key, and generating, by a key management unit, a backup key included in the distributed key;
   generating, by the user terminal, first encrypted medical data by encrypting medical data with the user key, and transmitting the medical data and the first encrypted medical data to the user agent;
   generating, by the user agent, second encrypted medical data by encrypting the medical data received from the user terminal with the agent key, generating final encrypted medical data using the first encrypted medical data and the second encrypted medical data, and storing the final encrypted medical data in a medical database; and
   generating, by the user agent, a hash value of the received medical data and storing the hash value of the received medical data in a medical blockchain.

2. The method of claim 1, wherein the medical data includes at least one of health checkup data of the user, a prescription of the user, genetic analysis information of the user, exercise information of the user, hospital care data of the user, and lifelog information of the user.

3. The method of claim 1, further comprising:
   when a query of stored medical data is requested by the user terminal, generating, by the user agent, second decrypted medical data by decrypting the final encrypted medical data stored in the medical database with the agent key, and transmitting, to the user terminal, the second decrypted medical data and the final encrypted medical data; and
   when the second decrypted medical data and the final encrypted medical data are received, generating, by the user terminal, first decrypted medical data by decrypting the final encrypted medical data with the user key, and obtaining decrypted medical data using the first decrypted medical data and the second decrypted medical data.

4. The method of claim 1, further comprising:
   transmitting, by a hospital agent, a record request from a hospital to the user agent;
   inquiring, by the user agent, of the user terminal about the record request, and transmitting, to the hospital agent, a verifiable credential of the user consenting to recording when a permission for the record request is received from the user terminal;
   identifying, by the hospital agent, the user through the verifiable credential of the user, and transmitting additional medical data of the user to the user agent when the additional medical data is received from the hospital;
   transmitting, by the user agent, the additional medical data to the user terminal, and generating second encrypted additional medical data by encrypting the additional medical data with the agent key;
   generating, by the user terminal, first encrypted additional medical data by encrypting the additional medical data with the user key, and transmitting the first encrypted additional medical data to the user agent; and
   generating, by the user agent, final encrypted additional medical data using the first encrypted additional medical data and the second encrypted additional medical data, storing the final encrypted additional medical data in the medical database, generating a hash value of the additional medical data and storing the hash value of the additional medical data in the medical blockchain.

5. The method of claim 1, further comprising:
   transmitting, by a hospital agent, a query request for medical information of the user from a hospital to the user agent;
   inquiring, by the user agent, of the user terminal about the query request for medical information, and transmitting, to the hospital agent, a verifiable credential of the user consenting to the query request for medical information when a permission for the query request for medical information is received from the user terminal;

identifying, by the hospital agent, the user through the verifiable credential, and requesting medical data of the user from the user agent;

transmitting, by the user agent, the final encrypted medical data to the user terminal when the medical data of the user is requested by the hospital agent;

generating, by the user terminal, first decrypted medical data by decrypting the final encrypted medical data with the user key, and transmitting the first decrypted medical data to the user agent; and generating, by the user agent, second decrypted medical data by decrypting the final encrypted medical data with the agent key, obtaining decrypted medical data using the first decrypted medical data and the second decrypted medical data, and transmitting the decrypted medical data to the hospital agent.

6. The method of claim 1, further comprising:

transmitting, by a clinical agent, clinical trial information to all user agents when the clinical trial information is received;

transmitting, by the user agent, the final encrypted medical data to the key management unit when the clinical trial information is received;

generating, by the key management unit, first decrypted medical data by decrypting the final encrypted medical data with the backup key, and transmitting the first decrypted medical data to the user agent;

generating, by the user agent, second decrypted medical data by decrypting the final encrypted medical data with the agent key, and obtaining decrypted medical data using the first decrypted medical data and the second decrypted medical data;

identifying, by the user agent, whether the user is included in a clinical trial subject required in the clinical trial information using the decrypted medical data;

inquiring, by the user agent, of the user terminal whether to participate in a clinical trial when the user is included in the clinical trial subject; and transmitting, by the user agent, a verifiable credential of the user or the decrypted medical data to the clinical agent when a response indicating participation in the clinical trial is received from the user terminal.

7. The method of claim 6, further comprising:

transmitting, by the clinical agent, an end message according to an end of the clinical trial to the user agent when the end message is received; and transmitting, by the user agent, the end message to the user terminal when the end message is received.

8. The method of claim 6, wherein the clinical trial information includes at least one of a clinical trial subject condition, a clinical trial description, a clinical trial period, a clinical trial risk, and clinical trial participation fee information.

9. The method of claim 6, wherein the inquiring, by the user agent, of the user terminal whether to participate in the clinical trial when the user is included in the clinical trial subject comprises inquiring, by the user agent, of the user terminal whether to participate in the clinical trial, when the user is included in the clinical trial subject and when the clinical trial is included in a permitted clinical trial item preset by the user.

10. A non-transitory processor-readable medium having instructions stored thereon, which when executed by one or more processors, cause the one or more processors to implement a method for managing medical information, the method comprising:

generating, by a user terminal, a user key included in a distributed key, generating, by a user agent, an agent key included in the distributed key, and generating, by a key management unit, a backup key included in the distributed key;

generating, by the user terminal, first encrypted medical data by encrypting medical data with the user key, and transmitting the medical data and the first encrypted medical data to the user agent;

generating, by the user agent, second encrypted medical data by encrypting the medical data received from the user terminal with the agent key, generating final encrypted medical data using the first encrypted medical data and the second encrypted medical data, and storing the final encrypted medical data in a medical database; and generating, by the user agent, a hash value of the received medical data and storing the hash value of the received medical data in a medical blockchain.

11. The non-transitory processor-readable medium of claim 10, wherein the medical data includes at least one of health checkup data of the user, a prescription of the user, genetic analysis information of the user, exercise information of the user, hospital care data of the user, and lifelog information of the user.

12. The non-transitory processor-readable medium of claim 10, wherein the method further comprises:

when a query of stored medical data is requested by the user terminal, generating, by the user agent, second decrypted medical data by decrypting the final encrypted medical data stored in the medical database with the agent key, and transmitting, to the user terminal, the second decrypted medical data and the final encrypted medical data; and when the second decrypted medical data and the final encrypted medical data are received, generating, by the user terminal, first decrypted medical data by decrypting the final encrypted medical data with the user key, and obtaining decrypted medical data using the first decrypted medical data and the second decrypted medical data.

13. The non-transitory processor-readable medium of claim 10, wherein the method further comprises:

transmitting, by a hospital agent, a record request from a hospital to the user agent;

inquiring, by the user agent, of the user terminal about the record request, and transmitting, to the hospital agent, a verifiable credential of the user consenting to recording when a permission for the record request is received from the user terminal;

identifying, by the hospital agent, the user through the verifiable credential of the user, and transmitting additional medical data of the user to the user agent when the additional medical data is received from the hospital;

transmitting, by the user agent, the additional medical data to the user terminal, and generating second encrypted additional medical data by encrypting the additional medical data with the agent key;

generating, by the user terminal, first encrypted additional medical data by encrypting the additional medical data with the user key, and transmitting the first encrypted additional medical data to the user agent; and generating, by the user agent, final encrypted additional medical data using the first encrypted additional medical data and the second encrypted additional medical data, storing the final encrypted additional medical data in the medical database, generating a hash value of the additional medical data and storing the hash value of the additional medical data in the medical blockchain.

14. The non-transitory processor-readable medium of claim 10, wherein the method further comprises:
transmitting, by a hospital agent, a query request for medical information of the user from a hospital to the user agent;
inquiring, by the user agent, of the user terminal about the query request for medical information, and transmitting, to the hospital agent, a verifiable credential of the user consenting to the query request for medical information when a permission for the query request for medical information is received from the user terminal;
identifying, by the hospital agent, the user through the verifiable credential, and requesting medical data of the user from the user agent;
transmitting, by the user agent, the final encrypted medical data to the user terminal when the medical data of the user is requested by the hospital agent;
generating, by the user terminal, first decrypted medical data by decrypting the final encrypted medical data with the user key, and transmitting the first decrypted medical data to the user agent; and
generating, by the user agent, second decrypted medical data by decrypting the final encrypted medical data with the agent key, obtaining decrypted medical data using the first decrypted medical data and the second decrypted medical data, and transmitting the decrypted medical data to the hospital agent.

15. The non-transitory processor-readable medium of claim 10, wherein the method further comprises:
transmitting, by a clinical agent, clinical trial information to all user agents when the clinical trial information is received;
transmitting, by the user agent, the final encrypted medical data to the key management unit when the clinical trial information is received;
generating, by the key management unit, first decrypted medical data by decrypting the final encrypted medical data with the backup key, and transmitting the first decrypted medical data to the user agent;
generating, by the user agent, second decrypted medical data by decrypting the final encrypted medical data with the agent key, and obtaining decrypted medical data using the first decrypted medical data and the second decrypted medical data;
identifying, by the user agent, whether the user is included in a clinical trial subject required in the clinical trial information using the decrypted medical data;
inquiring, by the user agent, of the user terminal whether to participate in a clinical trial when the user is included in the clinical trial subject; and
transmitting, by the user agent, a verifiable credential of the user or the decrypted medical data to the clinical agent when a response indicating participation in the clinical trial is received from the user terminal.

16. The non-transitory processor-readable medium of claim 15, wherein the method further comprises:
transmitting, by the clinical agent, an end message according to an end of the clinical trial to the user agent when the end message is received; and
transmitting, by the user agent, the end message to the user terminal when the end message is received.

17. The non-transitory processor-readable medium of claim 15, wherein the clinical trial information includes at least one of a clinical trial subject condition, a clinical trial description, a clinical trial period, a clinical trial risk, and clinical trial participation fee information.

18. The non-transitory processor-readable medium of claim 15, wherein the inquiring, by the user agent, of the user terminal whether to participate in the clinical trial when the user is included in the clinical trial subject comprises inquiring, by the user agent, of the user terminal whether to participate in the clinical trial, when the user is included in the clinical trial subject and when the clinical trial is included in a permitted clinical trial item preset by the user.

* * * * *